(12) United States Patent
Larsen

(10) Patent No.: US 6,708,363 B2
(45) Date of Patent: Mar. 23, 2004

(54) INFANT PACIFIER CLEANING CONTAINER

(76) Inventor: L. Chris Larsen, 9520 E. Monte Ave., Mesa, AZ (US) 85212

( * ) Notice: Subject to any disclaimer, the term of this patent is extended or adjusted under 35 U.S.C. 154(b) by 132 days.

(21) Appl. No.: 10/155,846

(22) Filed: May 23, 2002

(65) Prior Publication Data

US 2003/0217423 A1 Nov. 27, 2003

(51) Int. Cl.[7] ................................................ B08B 1/00
(52) U.S. Cl. ...................... 15/104.92; 15/160; 15/210.1
(58) Field of Search ............................. 15/104.92, 160, 15/210.1, 21.1; 134/201, 117; D32/40

(56) References Cited

U.S. PATENT DOCUMENTS

| | | | |
|---|---|---|---|
| 4,329,996 A | 5/1982 | Copeland | 128/359 |
| 5,298,077 A * | 3/1994 | Saarela et al. | 134/6 |
| 5,402,810 A | 4/1995 | Donley | 134/135 |
| 5,722,537 A | 3/1998 | Sigler | 206/205 |
| 5,964,784 A | 10/1999 | Wang | 606/234 |
| 6,134,736 A | 10/2000 | Pankow | 15/104.92 |

\* cited by examiner

Primary Examiner—Deborah Jones
Assistant Examiner—Abraham Bahta
(74) Attorney, Agent, or Firm—Stoel Rives LLP

(57) ABSTRACT

A pacifier cleaner is disclosed that includes a container and a pacifier cleaner insert removably held in the container. The container encloses the pacifier while also holding a liquid for cleaning the pacifier. The insert is adapted to clean the nipple and the inside surface of the pacifier base while wet with a cleaning liquid distributed in the container. The insert may have clustered bristles, fingerlike extensions or flocked fibers. The pacifier base cleaning surface may have a convex shape to correspond with the shape of an inside surface of a pacifier base.

21 Claims, 4 Drawing Sheets

INFANT PACIFIER CLEANING CONTAINER

TECHNICAL FIELD

The present invention relates to a portable infant pacifier cleaning container that can be used to disinfect an infant pacifier.

BACKGROUND OF THE INVENTION

When an infant pacifier is dropped, infants often still want the pacifier again even though it has not been sterilized. For a variety of reasons, it may not be possible to immediately clean the pacifier. This can be very frustrating for an infant. Accordingly, there is a need for a portable device that enables an infant pacifier to be cleaned at any location.

Infant pacifiers are often stored in diaper bags or purses. Neither a diaper bag or a purse provides a sterile storage environment. There is a need for a portable device that enables an infant pacifier to be stored in a relatively sterile environment.

U.S. Pat. No. 5,722,537 issued to Sigler discloses a sponge held within a container that enables the nipple of a pacifier to be cleaned. However, the sponge is not adapted to clean the entire interior side of the base of the pacifier. This surface should be cleaned since the interior side of the base contacts the infant's mouth. Another disadvantage of the device disclosed in U.S. Pat. No. 5,722,537 is it that a pacifier cannot be securely stored in the device.

U.S. Pat. No. 5,402,810 issued to Donley discloses a pacifier storage and washing apparatus. However, the apparatus is not adapted to scrub the nipple of the pacifier or the interior side of the base of the pacifier that contacts the infant's mouth.

There is a need for a portable infant pacifier cleaner adapted to clean the entire interior side of the base of the pacifier and the nipple of the pacifier.

SUMMARY OF THE INVENTION

It is an object of the invention to provide a portable infant pacifier cleaner that enables an infant pacifier to be cleaned at any location.

It is another object of the invention to provide a portable infant pacifier cleaner that enables an infant pacifier to be stored in a relatively sterile environment.

It is an additional object of the invention to provide a portable infant pacifier cleaner adapted to clean the entire interior side of the base of the pacifier and the nipple of the pacifier by scrubbing these surfaces while the surfaces are wet with a cleaning liquid.

These objects are achieved by a pacifier cleaner that includes a container and a pacifier cleaner insert. The container is adapted to contain a pacifier and to hold a liquid for cleaning a pacifier. The insert is configured to cooperate with the container so that the insert can be removably held in the container.

The insert may comprise at least two components. For example, the insert may include a top component and a bottom component. The insert has a nipple aperture and a nipple chamber adapted to receive the entire nipple. The insert may also be integrally formed from a material such as an elastomeric material or a foam material.

The insert has a pacifier base cleaning surface that is adapted to clean an inside surface of a pacifier base. The insert also has a nipple cleaning surface that is adapted to contact a nipple of a pacifier along the length of the nipple. Examples of pacifier base cleaning surfaces and nipple cleaning surfaces include the terminal ends of clustered bristles, fingerlike extensions and flocked fibers. Extensions from an insert such as clustered bristles, fingerlike extensions and flocked fibers are advantageous as they can be wetted as a liquid for cleaning a pacifier is distributed in the container. The wet cleaning surfaces can then be used to scrub the pacifier base and the nipple of the pacifier while wet with a cleaning liquid. Note that the insert is configured to enable a cleaning fluid held in the container to be distributed throughout the container and into contact with the nipple cleaning surface and the pacifier base cleaning surface as the container is moved or even shaken.

The pacifier base cleaning surface may have a convex shape to correspond with the shape of an inside surface of a pacifier base. The convex shape enables the pacifier base cleaning surface to more easily clean the inside surface of a pacifier base. The pacifier base cleaning surface has a shape and circumference that is larger than the typical inside surface of a pacifier base so that the entire inside surface of the pacifier base is contacted.

In summary, these features of the portable infant pacifier cleaner provide several advantages. The infant pacifier cleaner enables an infant pacifier to be cleaned at any location and to be stored in a relatively sterile environment. The mentioned features also enable the entire interior side of the base of the pacifier and the nipple of the pacifier to be scrubbed while these surfaces are wet with a cleaning liquid.

Additional aspects and advantages of this invention will be apparent from the following detailed description of preferred embodiments thereof, which proceeds with reference to the accompanying drawings.

DETAILED DESCRIPTION OF PREFERRED EMBODIMENTS

Figure 1:
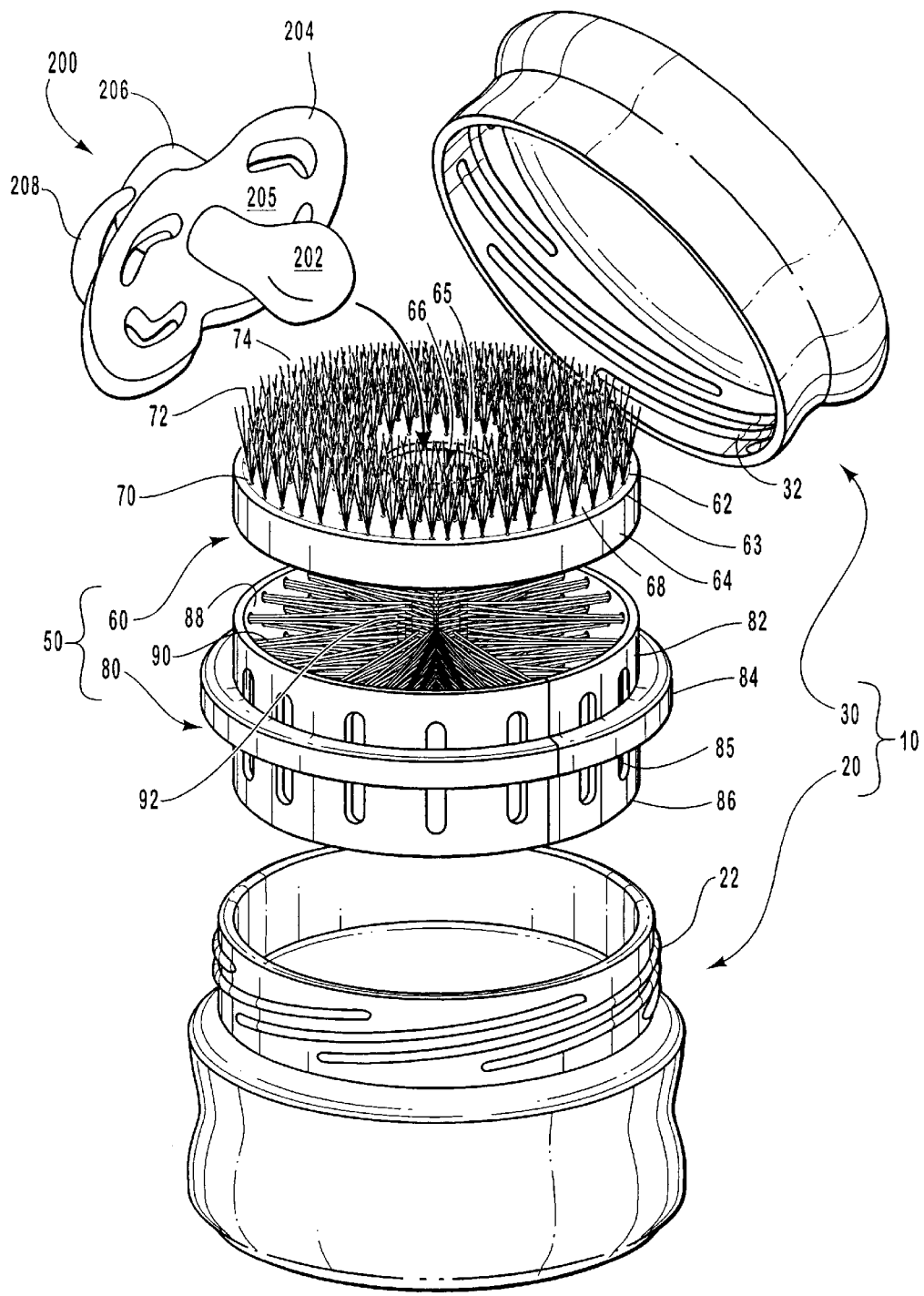
FIG. 1 is an exploded perspective view of an embodiment of an infant pacifier cleaning container.
Figure 2:
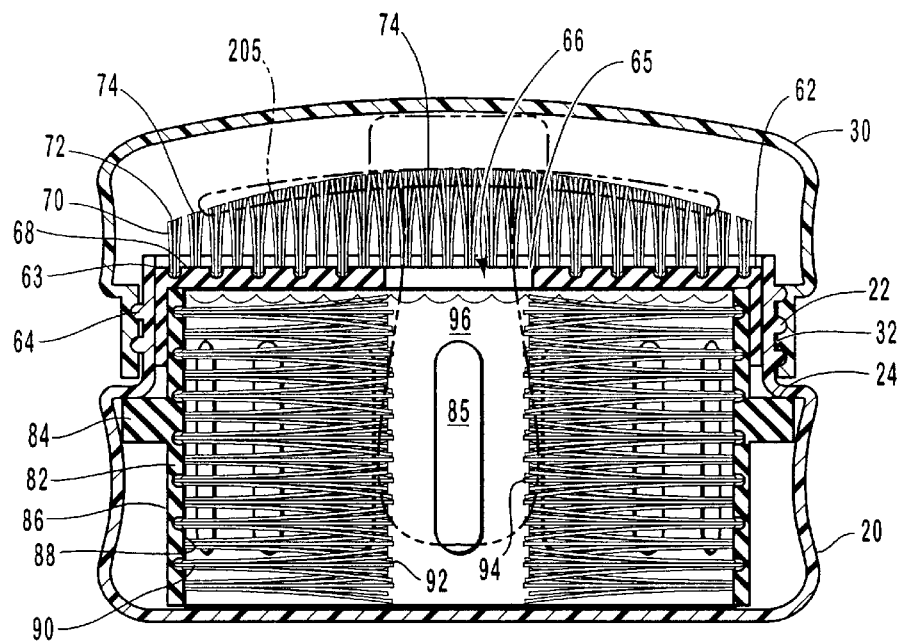
FIG. 2 is a cross-sectional view of the embodiment of the pacifier cleaning container shown in FIG. 1 with a pacifier stored in the container.
Figure 3:
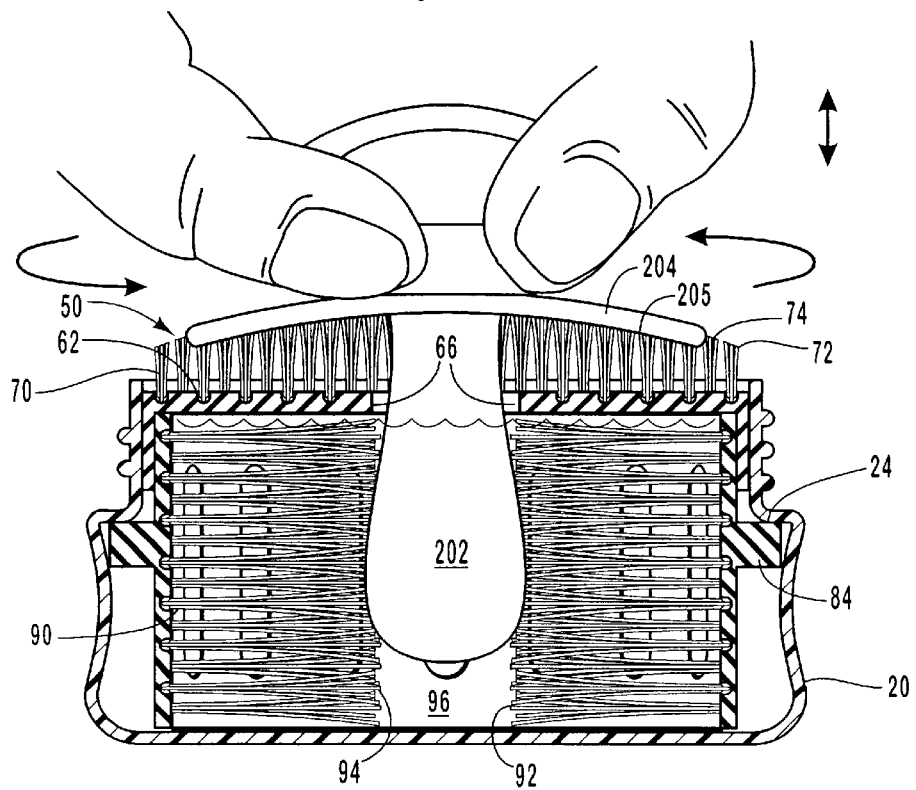
FIG. 3 is a cross-sectional view of the embodiment of the pacifier cleaning container shown in FIGS. 1–2 being cleaned against a removable cleaning insert. The removable cleaning insert has clusters of bristles.

FIGS. 1–3 show a pacifier 200 as used with a pacifier cleaning container 10. Pacifier 200 is representative of a conventional pacifier. Pacifier 200 has a nipple 202, a base 204, a plug 206 and a handle 208.

The main components of the pacifier cleaning container 10 include a container base 20, a container lid 30 and a pacifier cleaner insert 50. FIGS. 4–7 depict other inserts respectively at 50', 50", 150 and 150'. FIG. 7 also depicts another embodiment of a container base 20' and container lid 30'.

The container base 20 and container lid 30 depicted in FIG. 1 are adapted to be coupled together. More particularly, container lid 30 is adapted to be secured onto container base 20. Container base 20 has external threads 22 that mate with the internal thread 32 of lid 30. Container base 20 and container lid 30 are adapted to engage each other as pacifier 200 is contained within container 10 so that container 10 can be moved or even shaken while holding a cleaning liquid to distribute the cleaning liquid.

Pacifier cleaning container 10 shown in FIG. 1 has a two component cleaner insert 50. Insert 50 has a top component 60 and a bottom component 80. Top component 60 has a platform 62 with a skirt 64 extending downward from its outer perimeter 63. The inner perimeter 65 of the platform 62 defines a nipple aperture 66.

A plurality of clustered bristles 70 extend from a top surface 68 of platform 62. The terminal ends 72 of the bristles 70 comprise a pacifier base cleaning surface 74. As best seen in FIGS. 2–3, bristles 70 are arranged so that the pacifier base cleaning surface 74 is convex to correspond with the inside surface of a pacifier base which is typically curved or more specifically is typically concave as shown at 205.

As shown in FIG. 2, skirt 64 fits around barrel wall 82 of bottom component 80 so that top component 60 does not move relative to bottom component 80 once top component 60 is positioned on bottom component 80. A retention flange 84 extends from barrel wall 82 which engages a shoulder 24 of container base 20 as shown in FIGS. 2–3. Engagement between shoulder 24 and retention flange 84 enables insert 50 to be removably held in the container base. Bottom component 80 also has flow slots 85.

Bottom component 80 has an exterior surface 86 and an interior surface 88. A plurality of clustered bristles 90 extend from interior surface 88. Bristles 90 extend radially inward. The terminal ends 92 of bristles 90 comprise a nipple cleaning surface 94. The nipple cleaning surface 94 defines a nipple chamber 96. The nipple cleaning surface is adapted to contact a nipple 202 of a pacifier 200 along the length of the nipple 202. Note that the nipple chamber 96 has a length that essentially corresponds with the length of nipple 202 of pacifier 200. Note also that nipple chamber 96 has a diameter that approximately corresponds with the diameter of nipple aperture 66 in platform 62.

FIG. 3 shows nipple 200 being cleaned. Note that bristles 70 extend across platform 62 in a configuration such that the pacifier base cleaning surface 74 has a larger perimeter than pacifier base 204. The larger size of the pacifier base cleaning surface 74 allows the entire inside surface 205 of pacifier base 204 to be contacted. Rotation of pacifier 200, preferably with downward pressure of the pacifier against bristles 70, enables the inside surface 205 of pacifier base 204 to be scrubbed.

The diameter of nipple chamber 96 is slightly smaller than the diameter or width of pacifier nipple 202 at its greatest girth. The relative diameters enable nipple 202 to be scrubbed by bristles 90 as pacifier 200 is rotated and/or moved up and down against bristles 90.

Insert 50 is adapted to be wetted with a liquid for cleaning a pacifier. The container base 20 can hold liquid up to its rim. After container lid 30 is secured on container base 20 then container 10 can be moved or even shaken to distribute the liquid held in container base 20. The liquid passes primarily through flow slots 85 and nipple aperture 66 to the area defined by container lid 30. Shaking container 10 allows the entire pacifier 200 to be immersed in a cleaning liquid. However, the primary purpose in distributing the cleaning liquid is ensuring that bristles 70 are wetted despite being above the level of the liquid in container base 20 when container 10 is at rest as depicted in FIG. 2. Once bristles 70 have been wetted, pacifier 200 can be cleaned by scrubbing inside surface 205 of pacifier base 204 with bristles 70 and by scrubbing nipple 202 with bristles 90. Note bristles 70 and 90 may be either immersed or wetted depending on the orientation of container 10. The scrubbing action ensures that no debris remains on nipple 202 or on inside surface 205 of pacifier 200.

The cleaning liquid may be just water, however, the cleaning liquid is preferably a disinfecting liquid comprising water and a disinfectant or an antibacterial agent. Examples of suitable antibacterial agents include benzylkonium chloride and cetyl pyridinium. The combination of the scrubbing action with the use of a disinfecting liquid ensures that the pacifier is physically and chemically cleaned. This provides a significant advantage over prior pacifier cleaning systems that merely expose all or part of a pacifier to an antibacterial composition or that scrub only the nipple.

Figure 4:
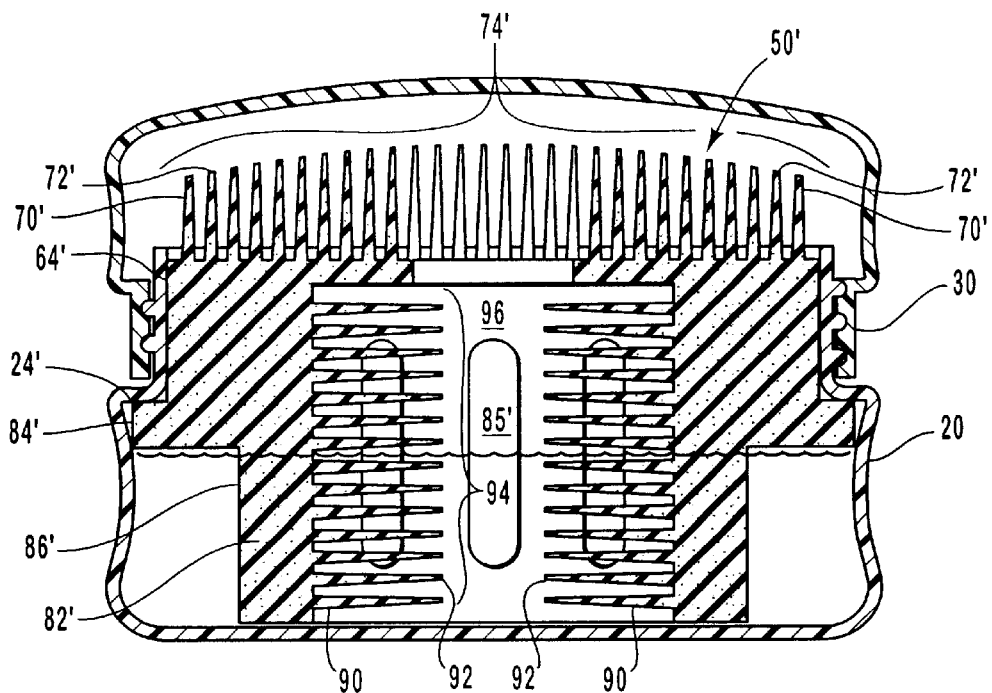
FIG. 4 is a cross-sectional view of a different embodiment of the pacifier cleaning container with a pacifier stored in the container. The removable cleaning insert has fingerlike extensions.

FIG. 4 depicts another embodiment of an insert identified at 50'. Insert 50' is an example of an insert that is integrally formed. Insert 50' has a skirt 64' above a retention flange 84' which extends from the exterior surface 86' of insert 50' to engage shoulder 24 of container base 20. Barrel wall 82' extends perpendicularly relative to retention flange 84' with a reduced thickness compared to skirt 64'. Insert 50' has flow slots 85' that allow cleaning fluid to move within container 10.

Fingers 70' and 90' extend respectively from a top surface 68' of platform 62' and from interior surface 88'. The terminal ends 92' of fingers 90' comprise a nipple cleaning surface 94 which defines a nipple chamber 96'. Unlike insert 50, nipple chamber 96' has a smaller diameter than the nipple aperture 66' defined by the inner perimeter 65' of platform 62'. Nipple chamber 96' is smaller as the fingers tend to be softer than the clustered bristles. The clustered bristles are typically formed from nylon while the fingers are typically formed from polyethylene.

Like insert 50, each finger 70' has a terminal end 72'. The terminal ends 72' of fingers 70' collectively comprise a convex pacifier base cleaning surface 74'. While this convex configuration is advantageous for cleaning concave inside surfaces of a pacifier base, other embodiments may have a flat configuration. Both convex and flat configurations can be used to clean inside surfaces of a pacifier base which is either concave or flat by use of varying amounts of force.

Figure 5:
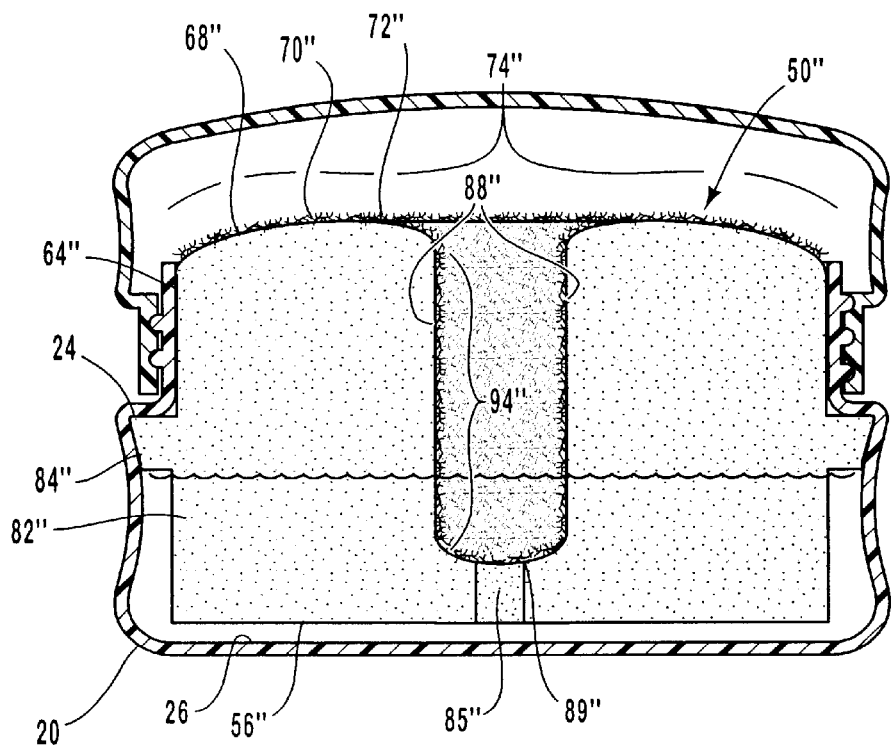
FIG. 5 is a cross-sectional view of an additional embodiment of the pacifier cleaning container with a pacifier stored in the container. The removable cleaning insert is an integral component that has been flocked with fibers.

FIG. 5 depicts another integral insert identified at 50". Insert 50" is integrally formed from an elastomeric material. Insert 50" has an exterior surface that is a closed skin of the elastomeric material. The insert may be merely the elastomeric material by itself. However, the elastomeric material is advantageously covered with fibers to clean the pacifier surfaces. Insert 50" is shown with fibers on its surfaces as identified at 70" and 90". More particularly, the surfaces of the insert that contact pacifier 200, the top surface 68" and the interior surface 88" of inset 50", have been flocked with fibers. The insert may be flocked with fibers by any conventional methodology.

Insert 50" has a retention flange 84" which extends from the exterior surface of insert 50" to engage shoulder 24 of container base 20. Retention flange 84" extends perpendicularly between skirt 64" and barrel wall 82". The flexibility of insert 50" enables retention flange 84" to flex into position within container base 20 below shoulder 24.

Each fiber 70" has a terminal end 72". The terminal ends 72" collectively comprise a pacifier base cleaning surface 74". Note that pacifier base cleaning surface 74" is only slightly convex. However, pacifier base cleaning surface 74" may be significantly more convex or flat depending on the shape of top surface 68".

The terminal ends 92" of fibers 90" comprise another example of a nipple cleaning surface 94" which defines a nipple chamber 96". Unlike the other nipple chambers discussed above, nipple chamber 96" is adapted to clean the distal tip of nipple 202 through contact with fibers at the bottom of chamber 96". More particularly, interior surface 88" of insert 50" includes a concave bottom surface 89" which is coated with flocked fibers 90". This configuration enables the distal tip of nipple 202 to be cleaned without relying on the contact between the distal tip of the nipple and the sides of the nipple cleaning surface as the nipple 202 is pushed downward.

Insert 50" is not shown with flow slots, however, it may also be configured with flow slots. Insert 50" has a flow portal 85" that extends from bottom surface 89" through insert 50" to the bottom 56" of the insert 50 above bottom 26 of the interior surface of container base 20. Flow portal 85" and flow slots 85 and 85' of the other embodiments are examples of flow openings adapted to allow the cleaning liquid to move into nipple chamber 96". Note that bottom 56" is slightly offset from bottom 26 of the interior surface of container base 20 so that the cleaning liquid can easily flow into flow portal 85".

Of course, the other embodiments can also be modified to ensure that the distal end of pacifier nipple 202 is more easily cleaned without brushing nipple 202 against nipple cleaning surfaces that form part of the inserts. For example, clustered bristles or fingers may extend from the interior surface of the bottom of container base 20 at a position suitable for cleaning the distal end of nipple 202.

Bristles 70 and 90, fingers 70' and 90', and fibers 70" and 90" of inserts 50, 50' and 50" are examples of scrubbing extensions that extend from surfaces of an insert and are adapted for cleaning pacifier surfaces. These extensions extend from a nonporous insert that is nonreticulated. The advantage of a nonporous insert with scrubbing extensions is the ability to wet the extensions with a liquid for cleaning a pacifier without using the interior of the insert as a reservoir to store the liquid.

Figure 6:
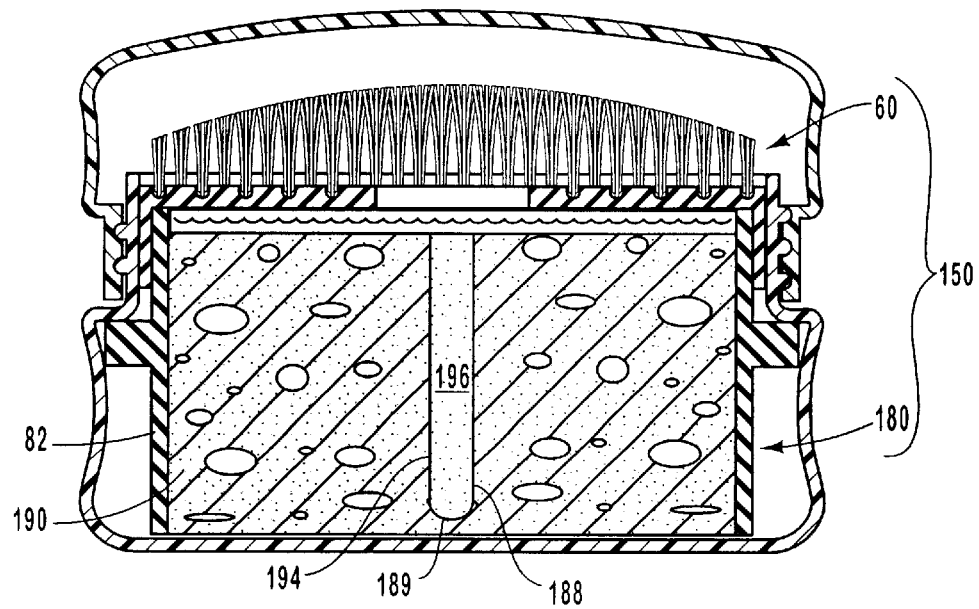
FIG. 6 is a cross-sectional view of another embodiment of the pacifier cleaning container with a pacifier stored in the container. The removable cleaning insert has two components, the top component has clusters of bristles and the bottom component is a sponge.
Figure 7:
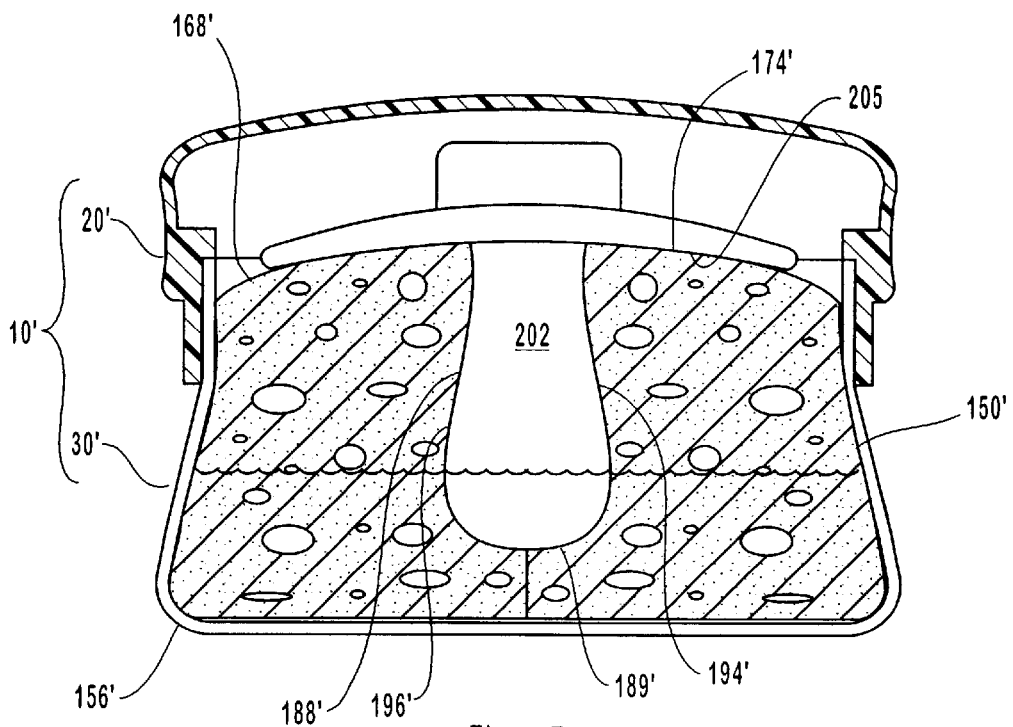
FIG. 7 is a cross-sectional view of yet another embodiment of the pacifier cleaning container with a pacifier stored in the container. The removable cleaning insert is a sponge.

FIG. 6 depicts another embodiments of an insert identified at 150. Insert 150 has two components. The top component 60 is identical to the top component 60 of insert 50 shown in FIGS. 1–3. The bottom component 180 has a barrel wall 82 that is nearly identical to barrel wall 82 shown in FIGS. 1–3 except that there are no bristles extending from interior surface 88.

A sponge 190 is held in barrel wall 82 under top component 60. Sponge 190 has an interior surface 188 that acts as a nipple cleaning surface 194. Nipple cleaning surface 194 defines a nipple chamber 196 which is essentially a slit in the sponge. Nipple chamber 196 has a length that essentially corresponds with the length of nipple 202. However, nipple chamber 196 has a width that in a relaxed state is significantly smaller than nipple 202 so that nipple 202 can be easily scrubbed by nipple cleaning surface 194. In order for nipple cleaning surface 194 to be wetted, it is necessary for sponge 190 to act as a reservoir for a cleaning liquid. This requires more cleaning liquid than the other embodiments with scrubbing extensions.

An advantage of the use of a sponge in this configuration is that the distal end of the pacifier nipple 202 is easily cleaned. More particularly, like insert 50" nipple chamber 196 has a concave bottom surface 189 which enables the distal tip of nipple 202 to be cleaned without relying on the contact between the distal tip of the nipple and the sides of the nipple cleaning surface as the nipple 202 is pushed downward.

FIG. 7 depicts a cross-sectional view of yet another embodiment of the pacifier cleaning container 10' and an insert 150'. Cleaning container 10' includes a container base 20' and a container lid 30' that are held together in a frictional fit. Insert 150' is held in container base 20' through reliance on a frictional fit. Insert 150' is a sponge that is shaped to have a slightly wider bottom 156' that at its top surface 168'.

Top surface 168' is the pacifier base cleaning surface 174'. Top surface 168' is convex for optimal ease in cleaning pacifier base 204. Of course, like the other embodiments, top surface 168' can also be flat.

Insert 150' has an interior surface 188' that acts as a nipple cleaning surface 194'. Nipple cleaning surface 194' defines a nipple chamber 196' which is essentially identical to nipple chamber 196. Like nipple chamber 196, nipple chamber 196' has a length that essentially corresponds with the length of nipple 202. Also nipple chamber 196' has a concave bottom surface 189'.

It will be obvious to those having skill in the art that many changes may be made to the details of the above-described embodiments of this invention without departing from the underlying principles thereof. The scope of the present invention should, therefore, be determined only by the following claims.

What is claimed is:

1. A pacifier cleaner for cleaning a pacifier comprising
    a container adapted to contain a pacifier and to hold a liquid for cleaning a pacifier, and
    a pacifier cleaner insert,
    wherein the insert is configured to cooperate with the container so that the insert can be removably held in the container,
    wherein the insert has a pacifier base cleaning surface that is adapted to clean an inside surface of a pacifier base, and
    wherein the insert has nipple cleaning surface that defines a nipple chamber and that is adapted to contact a nipple of a pacifier along the length of the nipple, wherein the nipple chamber has a length that essentially corresponds with the length of a nipple of a pacifier, and
    wherein the pacifier base cleaning surface and the nipple cleaning surface are both adapted to be wetted as a liquid for cleaning a pacifier is distributed in the container to the cleaning surfaces so that the pacifier base cleaning surface and the nipple cleaning surface can respectively scrub the pacifier base and the nipple of the pacifier while wet with the cleaning liquid.

2. A pacifier cleaner as recited in claim 1 wherein the container comprises a container base and a container lid and wherein the container lid and container base are adapted to engage each other so that the pacifier is contained within the container and the container can be moved while holding the cleaning liquid to distribute the cleaning liquid.

3. A pacifier cleaner as recited in claim 2 wherein the insert has a retention flange extending from a sidewall that engages a shoulder of the container base.

4. A pacifier cleaner as recited in claim 1 wherein the insert includes a top component and a bottom component.

5. A pacifier cleaner as recited in claim 1 wherein the insert is integrally formed.

6. A pacifier cleaner as recited in claim 1 wherein the insert is configured to enable a cleaning fluid held in the container to move throughout the container and into contact with the nipple cleaning surface and the pacifier base cleaning surface.

7. A pacifier cleaner as recited in claim 1 wherein the pacifier base cleaning surface has a convex shape to correspond with the shape of an inside surface of a pacifier base.

8. A pacifier cleaner for cleaning a pacifier comprising:
a container adapted to contain a pacifier and to hold a liquid for cleaning a pacifier, and
a pacifier cleaner insert that is nonporous to a liquid held in the container for cleaning the pacifier,
wherein the insert is configured to cooperate with the container so that the insert can be removably held in the container,
wherein the insert has a top surface from which a plurality of extensions extend, wherein the extensions have terminal ends that act as a pacifier base cleaning surface to clean an inside surface of a pacifier base,
wherein the insert has an interior surface from which a plurality of extensions extend, wherein the extensions have terminal ends that act as a nipple cleaning surface to clean a nipple of a pacifier along the length of the nipple, and
wherein the pacifier base cleaning surface and the nipple cleaning surface are both adapted to be wetted as a liquid for cleaning a pacifier is distributed in the container to the cleaning surfaces so that the pacifier base cleaning surface and the nipple cleaning surface can respectively scrub the pacifier base and the nipple of the pacifier while wet with the cleaning liquid.

9. A pacifier cleaner as recited in claim 8 wherein the container comprises a container base and a container lid and wherein the container lid and container base are adapted to engage each other so that the pacifier is contained within the container and the container can be moved while holding the cleaning liquid to distribute the cleaning liquid.

10. A pacifier cleaner as recited in claim 8 wherein the insert includes at least two separate components.

11. A pacifier cleaner as recited in claim 8 wherein the insert is integrally formed.

12. A pacifier cleaner as recited in claim 8 wherein the insert is configured to enable a cleaning fluid held in the container to move throughout the container and into contact with the nipple cleaning surface and the pacifier base cleaning surface.

13. A pacifier cleaner as recited in claim 8 wherein the pacifier base cleaning surface has a convex shape to correspond with the shape of an inside surface of a pacifier base.

14. A pacifier cleaner as recited in claim 8 wherein at least one of the plurality of extensions is a cluster of bristles.

15. A pacifier cleaner as recited in claim 8 wherein at least one of the plurality of extensions comprises fingerlike extensions.

16. A pacifier cleaner as recited in claim 8 wherein at least one of the plurality of extensions comprises flocked fibers.

17. A pacifier cleaner for cleaning a pacifier comprising:
a container adapted to contain a pacifier and to hold a liquid for cleaning a pacifier,
wherein the container includes a container base and a container lid, and
a pacifier cleaner insert configured to cooperate with the container so that the insert can be removably held in the container,
wherein the insert includes a top component and a bottom component,
wherein the top component has a platform that has a top surface and that defines a nipple aperture, wherein a plurality of clustered bristles extend from the top surface, wherein the clustered bristles have terminal ends that act as a pacifier base cleaning surface to clean an inside surface of a pacifier base,
wherein the bottom component has a sidewall with an interior surface from which a plurality of clustered bristles extend, wherein the clustered bristles have terminal ends that act as a nipple cleaning surface to clean a nipple of a pacifier along the length of the nipple, and
wherein the pacifier base cleaning surface and the nipple cleaning surface are both adapted to be wetted as a liquid for cleaning a pacifier is distributed in the container to the cleaning surfaces so that the pacifier base cleaning surface and the nipple cleaning surface can respectively scrub the pacifier base and the nipple of the pacifier while wet with the cleaning liquid.

18. A pacifier cleaner as recited in claim 17 wherein the top component has a skirt extending downward from the top platform at the outer perimeter of the platform, wherein the skirt fits around the sidewall of the bottom component container so that the top component does not move relative to the bottom component.

19. A pacifier cleaner as recited in claim 17 wherein the bottom component has a retention flange extending from the sidewall that engages a shoulder of the base container.

20. A pacifier cleaner as recited in claim 17 wherein the pacifier base cleaning surface has a convex shape to correspond with the shape of an inside surface of a pacifier base.

21. A pacifier cleaner as recited in claim 17 wherein the bottom component is configured to enable a cleaning fluid held in the container base to move throughout the container and into contact with the plurality of clustered bristles extending from the top surface of the top component and the plurality of clustered bristles extending from the interior surface of the sidewall of the bottom component.

* * * * *